United States Patent
Costa

(10) Patent No.: US 6,309,378 B1
(45) Date of Patent: Oct. 30, 2001

(54) SANITARY NAPKIN

(75) Inventor: Rogerio Costa, Lorena (BR)

(73) Assignee: Johnson & Johnson Ind. E Com. Ltda., Sao Paulo (BR)

( * ) Notice: Subject to any disclaimer, the term of this patent is extended or adjusted under 35 U.S.C. 154(b) by 0 days.

(21) Appl. No.: 09/371,173

(22) Filed: Aug. 11, 1999

(51) Int. Cl.[7] .................................................... A61F 13/15
(52) U.S. Cl. ..................... 604/385.04; 604/386; 604/387
(58) Field of Search .................. 604/385.01, 385.03, 604/385.04, 385.05, 385.201, 386, 387, 390, 389

(56) References Cited

U.S. PATENT DOCUMENTS

| | | |
|---|---|---|
| 4,596,570 | 6/1986 | Jackson et al. . |
| 4,864,828 | 9/1989 | Matheny et al. . |
| 4,917,697 * | 4/1990 | Osborn, III et al. ................. 604/387 |
| 5,330,461 * | 7/1994 | Leeker .............................. 604/385.2 |
| 5,520,676 | 5/1996 | Lavash et al. . |
| 5,643,245 | 7/1997 | Osborn, III et al. . |
| 5,669,898 | 9/1997 | Ahr . |
| 5,714,027 * | 2/1998 | Taub ..................................... 156/204 |
| 5,743,897 | 4/1998 | Niihara et al. . |
| 5,772,648 * | 6/1998 | Osborn, III et al. ............. 604/385.1 |
| 5,873,871 * | 2/1999 | Lavash et al. ....................... 604/386 |

FOREIGN PATENT DOCUMENTS

| | | |
|---|---|---|
| 0 464 855 A1 | 1/1992 | (EP) . |
| 0 607 090 A1 | 7/1994 | (EP) . |

* cited by examiner

*Primary Examiner*—John G. Weiss
*Assistant Examiner*—Jamisue Webb

(57) ABSTRACT

A sanitary napkin having an upper liquid permeable layer; a lower liquid impermeable layer; an absorbent body placed between the upper and lower layers; an impermeable top film over the lower layer; laterally extended wings that can be folded and lodged, in a rest position, between the lower layer and top film. The wings are releasably attached to the top film.

6 Claims, 3 Drawing Sheets

SANITARY NAPKIN

BACKGROUND OF THE INVENTION

The present invention is related to a, preferably disposable, sanitary napkin, and provided with side wings that can be used initially or during use, according to the will and convenience of the user.

As already known in the art, sanitary napkins are normally disposable and used to collect and contain vaginal exudates, especially menstrual blood, intermenstrual secretion and even urine in cases of incontinence.

Typically, such napkins are comprised of a generally oblong body made of absorbent material, wrapped between two layers, one of which is an upper permeable layer adapted to contact the user's body, and the other is a lower impermeable layer facing her under garment.

The permeable upper layer is adapted to contact the pelvic region of the user, and therefore it is generally made of a comfortable non-irritating material. According to the current state of the art, said layer can be a perforated plastic film, a porous or crosslinked foam, a sheet of woven or non-woven material provided with natural fibers (wood or cotton fibers), synthetic fibers (polyester or polypropylene), or even of a synthetic or natural fiber combination. The upper layer can be of hydrophobic material, thus tending to remain dry.

On the other hand, the function of the impermeable lower layer is to prevent the fluid absorbed and retained in the absorbent body from passing through towards the user's clothes or skin, and it is generally a fine polyethylene sheet. The lower layer may be vapor permeable, in which case it is provided with small pores or made of a material impermeable to liquids.

Prior art sanitary napkins frequently have one or more adhesive regions in the respective impermeable lower layers, generally in a central portion in the longitudinal and/or transverse direction thereof, in order to attach the napkin to the internal face of the crutch portion of the user's panties. The adhesive region may comprise a single area or a series of discrete areas, and the trend is to apply the adhesive to the lower layer along one or more longitudinal bands, to simplify the process of manufacture.

In its turn, the absorbent body may be made of any material able to absorb and retain body exudates such as, for example, wood pulp, paper, bamboo fibers, sugar cane husks, corn stem or cob, turf moss, absorbent foams or sponges, synthetic or polymeric fibers, super-absorbent materials (that form hidrogels when in contact with liquids), combinations of the materials above, and the like.

Currently, most sanitary napkins are provided with flexible wings that extend laterally, for example, as a prolongation of one or both of the upper and lower layers, with the function of attaching the napkin to the user's panties. For such, the wings are folded around the edges of the crutch portion of the panties, and face the external surface thereof. Preferably, one or more regions of the wings are coated with adhesives, thus allowing them to be attached to the panties for preventing displacement of the napkin when in use.

The adhesive regions are preferably located over the lower surface of the wing, which is usually a prolongation of the impermeable lower layer of the napkin.

The adhesive coated regions, either in the impermeable lower layer of the napkin, or in the respective wings, must be protected against any type of contact before the napkin is used, to avoid the risk of losing their adhesive properties or inadvertent adhesion to unsuitable parts of the user's napkin or clothes, in which case the napkin might be damaged due to the softness of the materials used in its manufacture.

For that purpose, protective sheets are frequently used, which sheets are also known as "release papers" and are comprised of a sheet of paper coated with anti-adhesive resin such as silicone, or the like, thus protecting the adhesive surface until it is used, at which time they are removed for exposing the adhesive.

DESCRIPTION OF THE ART

As to the prior art, reference can be made to U.S. Pat. No. 5,281,209 granted to Osborn and Lavash, wherein the wings of a sanitary napkin are folded and kept adhered to the lower surface of the napkin body, thus providing a rest position in which they will be held in a non-stable state if the user initially does not wish to use them.

For keeping said wings attached to the body of the napkin when they are not in use, recessed areas are provided over or inside the impermeable lower layer of the napkin, under which the wings are temporarily inserted. Such an arrangement producer a feeling of insecurity in the user since the wings could easily get out of position during use due to the movement of her body and possibly cause leakage.

U.S. Pat. No. 5,330,461 granted to Leeker can also be cited, this document disclosing a sanitary napkin provided with optionally usable wings, but the arrangement prevents the user from pulling the wings out during use, for part of the surface of the wing acts as a support for the product as a whole since the beginning of its use.

Mention can also be made of Swedish Patent SE9601688, granted to Hanssen and Trenk, which discloses a sanitary napkin provided with optionally usable wings. However, the option for non-use of the wings implies in the removal thereof, without possibility of a later use after the product has already having been put into use.

It is clear that the state of art does not provide any sanitary napkin having side wings that can be used optionally by the user even after the product is put to use, and does not cause discomfort or even leakage if the user decides not to use them.

OBJECTS OF THE INVENTION

One of the main objects of this invention is to provide a sanitary napkin provided with wings or tabs that can be used initially or at any time during use of the napkin.

Another object of the invention is a sanitary napkin provided with flexible folded side wings which can be releasably attached before use of the article.

Still another object of the invention is to provide a sanitary napkin having wings that remain folded during use until the user decides to use them, thus providing her with a feeling of security from undesirable leakages.

Such objects are attained by means of a sanitary napkin which is comprised of an upper liquid permeable layer; a lower liquid impermeable layer; an absorbent body placed between the upper and lower layers; an impermeable top film over the lower layer; laterally extendible foldable wings that can be lodged in a rest position between the lower layer and the top film. According to the invention, the wings are releasably attached at least to the top film.

As used herein, releasable attachment means the existence of suitable attaching means (glue, welding, sealing, crimping, and the like) that can be deliberately undone without significant damage to any of the previously attached underlying substrates.

An example of releasable attachment is the contact of a permanent touch adhesive (commonly known as "psa", the abbreviation for "pressure sensitive adhesives") over a substrate coated with a resin that permits non-permanent adherence.

Still another example of releasable attachment is that attained by crimping, which consists of pressing two or more layers of material against each other, in such a way that the interface between the two layers can provide a surface with protuberances and recesses for the inter-penetration between the respective materials, thus releasably attaching one layer to another.

BRIEF DESCRIPTION OF THE DRAWINGS

The present invention will be described below in greater details with reference to the accompanying drawings that represent non-limiting alternative embodiments, wherein.

Figure 1:
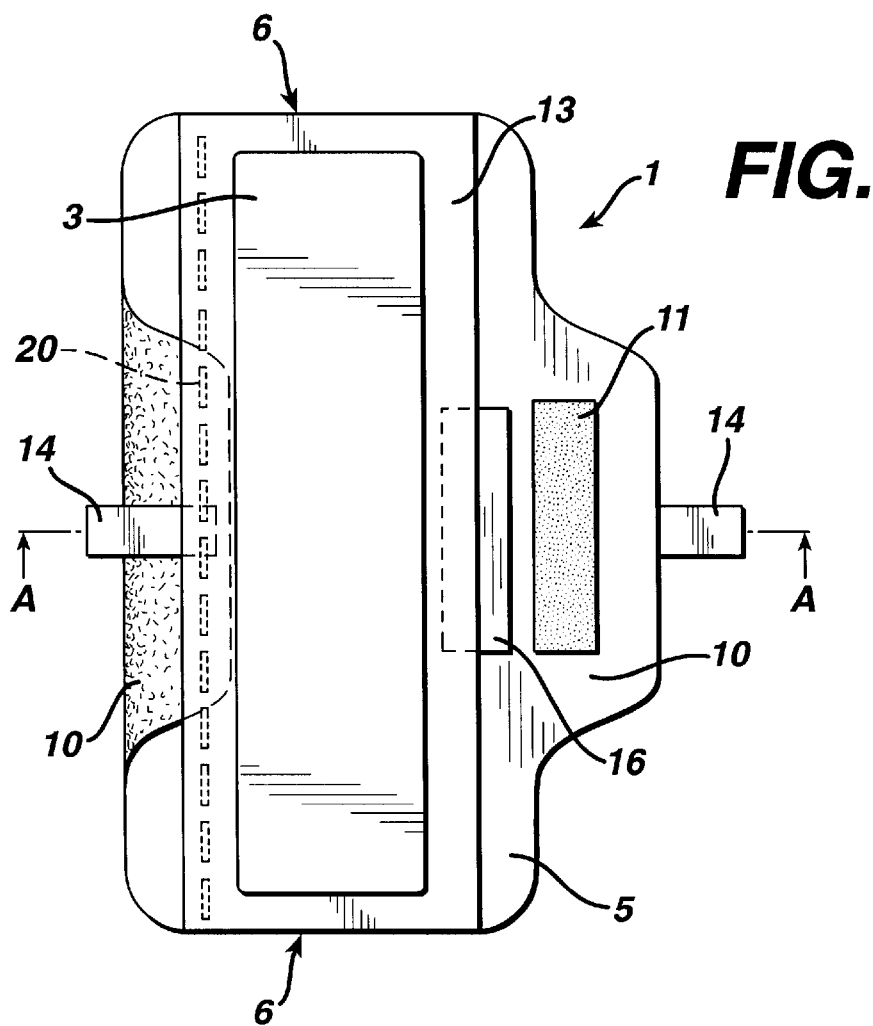
FIG. 1 is a top view of a sanitary napkin that represents a first preferred embodiment of the present invention.
Figure 1A:
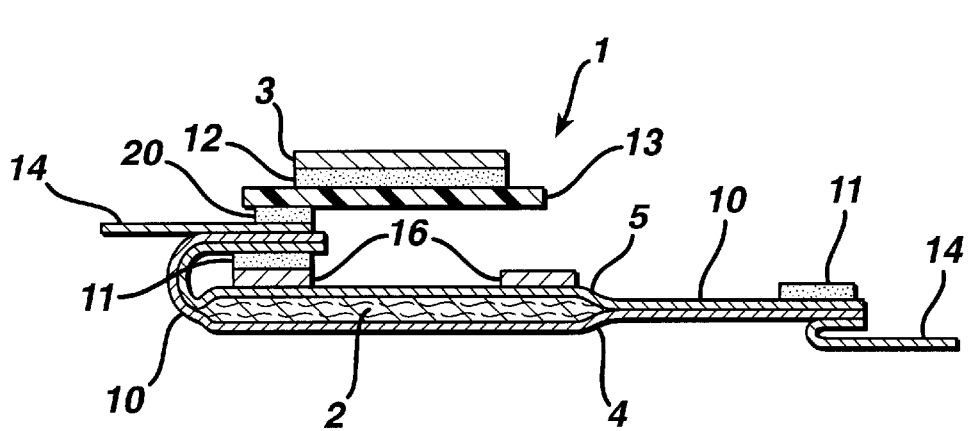
FIG. 1A is a cross-sectional view of FIG. 1, taken along line AA.

The left side of the figures show the situation in which the side wing is releasably attached to the sanitary napkin prior to use thereof, and the right side shows the situation in which the side wing has been dislodged from the rest position and is ready for use.

DETAILED DESCRIPTION OF THE FIGURES

As illustrated in FIGS. 1 to 4, sanitary napkin 1 comprises a substantially planar absorbent body 2 surrounded by a permeable upper layer 4 suited to contact the user's body and by an impermeable layer 5 facing the user's underclothes.

As known in the art, napkin 1 is also has flexible wings 10 that extends laterally as a prolongation of upper and lower layers 4 and 5, respectively. The lower face of each wing 10 is provided with a first adhesive region 11, allowing its attachment to the crutch portion of the user's panties, thus configuring an in-use position for the wings.

At least one impermeable top film 13 is provided, which extends longitudinally along at least part of lower layer 5. Film 13 is attached to lower layer 5 along lines 6 in such a way that it covers the ends of wings 10 when these are folded, thus configuring a corresponding rest position. A second adhesive region 12 can be provided in at least a longitudinal portion of film 13, being protected by a resin-coated protection sheet 3.

In accordance with a first preferred embodiment of this invention, as illustrated in FIG. 1, longitudinal adhesive bands 20 are provided, which bands are respectively adjacent to the edges of film 13. Each one of bands 20 provides for a releasable attachment of relevant wing 10 to film 13.

Bands 20 must be provided with length and width suitable to keep wing 10 steady. Thus, the length of said band 20 may vary, covering a longitudinal portion that may be shorter, equal or even longer than the portion for contact between said wing 10 and layer 13. Preferably, band 20 covers all the extension of contact between said wing 10 and layer 13 of napkin 1.

Sheets 16 for protecting adhesives 11 on lower layer 5 are also provided, which sheets are positioned in such a way that, when wings 10 are resting, the corresponding adhesive regions 11 releasably adhere to corresponding protective sheets 16. The use of said protection sheets 16 allows a partial adhesion of adhesive regions 11 to lower layer 5, in such a way that they do not lose its adhesive capacity when wings 10 are removed from their rest position.

Napkin 1 may also comprise additional protective sheets (not shown) between wings 10 and respective bands 20, the rest of each band 20 attaching film 13 to lower layer 5.

As illustrated in FIGS. 1 through 4, extensions 14 in the ends of wings 10 are provided so that the user can pull them out when using the sanitary napkin 1, said wings 10 then being available for being attached to the crutch portion of the outer face of the user's panties.

Figure 2:
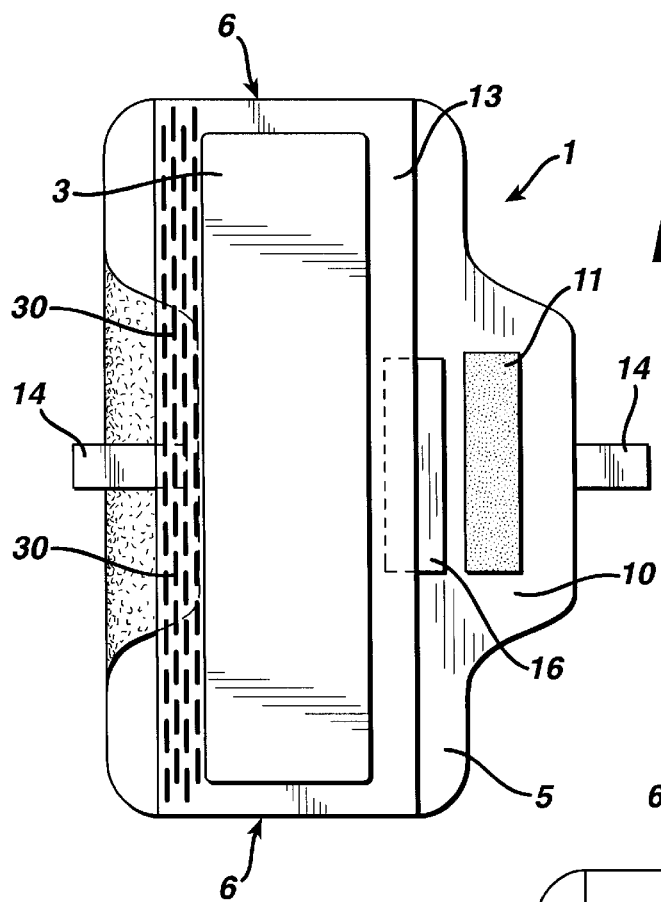
FIG. 2 is a top view of a sanitary napkin that represents a second preferred embodiment of the present invention.

In accordance with a second embodiment of the present invention, illustrated in FIG. 2, the attachment of wings 10 between lower layer 5 and top film 13 is accomplished by a crimping process, thus replacing adhesive band 20 with a crimping portion 30.

As shown, crimped portions 30 extend along the longitudinal edges of film 13, and they can have the same length as napkin 1.

As previously described, the user will have to pull extensions 14 whenever she wants to use wings 10 of napkin 1, thus releasing the crimped portion 30 that holds wings 10 in the rest position and freeing them for use.

Figure 3:
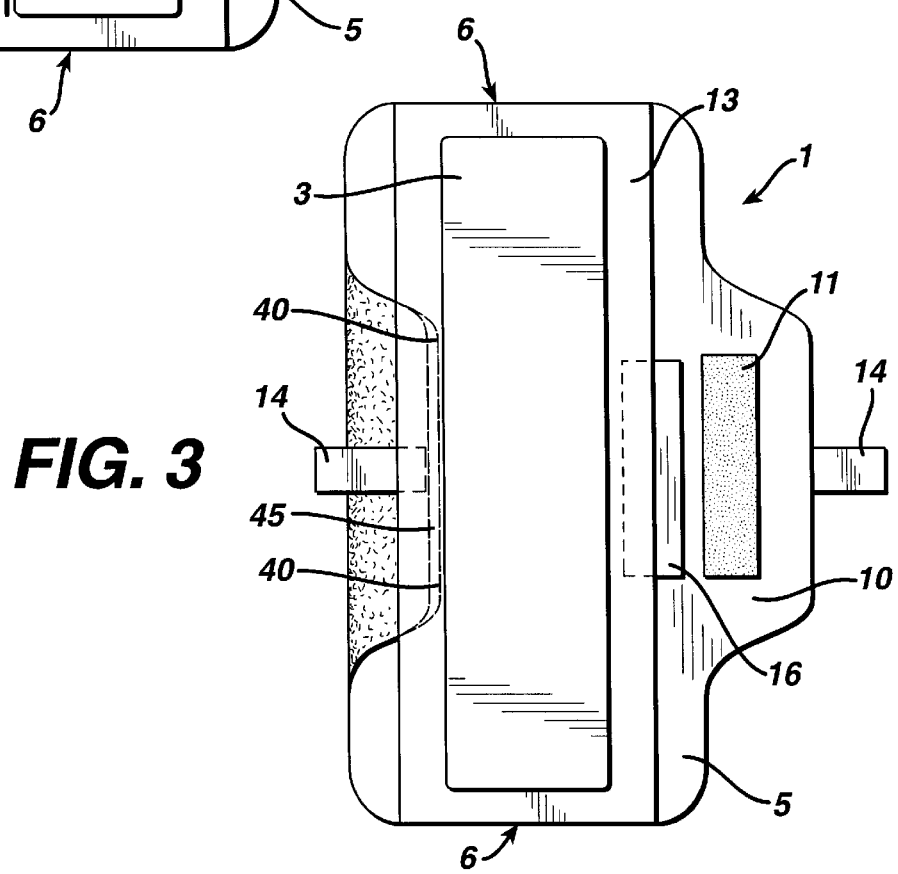
FIG. 3 is a top view of a sanitary napkin that represents a third preferred embodiment of the present invention.

In accordance with a third preferred embodiment of this invention, illustrated in FIG. 3, weakening lines 40 are provided, preferably as weakened or punched lines, in film 13, such lines delimiting detachable portions 45 of film 13 itself. Such detachable portions 45 are respectively attached in a non-detachable manner to wings 10 in their rest position. In this way, when the user pulls extensions 14, weakening lines 40 are broken, thus freeing wings 10 for use.

Figure 4:
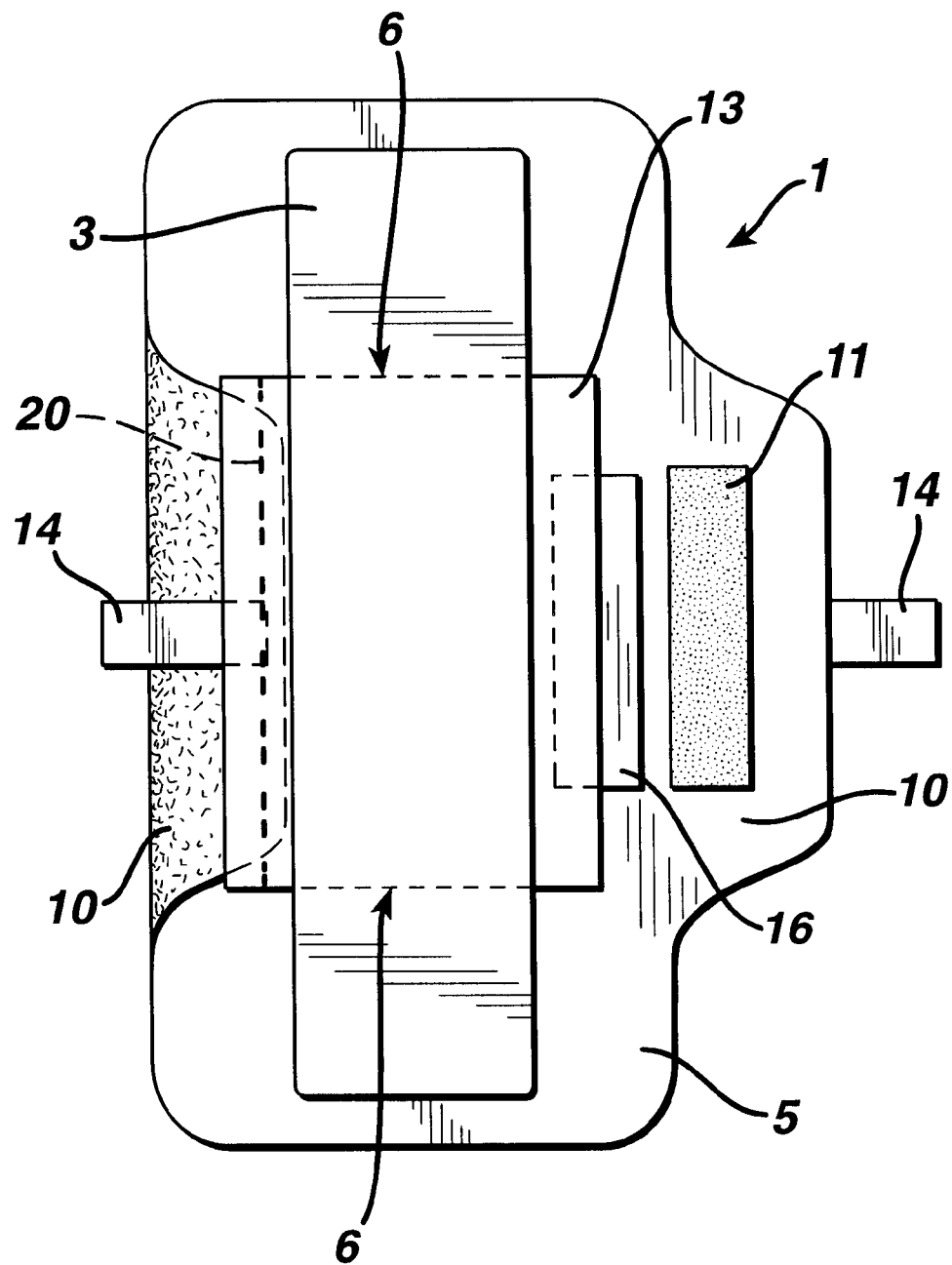
FIG. 4 is a top view of a sanitary napkin that represents a fourth preferred embodiment of the invention.

In accordance with a fourth embodiment of this invention, illustrated in FIG. 4, and maintaining a certain similarity with the first embodiment shown in FIG. 1, film 13 is shorter than the length of napkin 1. A band of glue, not shown, extends over lower layer 5 of napkin 1, going from a longitudinal end to the opposite one, except between lines 6, where said glue band covers the outer surface of film 13. Lines 6 are lines for attaching film 13 onto lower layer 5.

Various examples of preferred embodiments having been described, it is to be understood that the scope of the present invention encompasses other possible variations, it being limited only by the content of the accompanying claims, wherein possible equivalents are included.

What is claimed is:

1. A sanitary napkin having a length, comprising:

an upper liquid permeable layer;

a lower liquid impermeable layer;

an absorbent body between said upper and lower layers;

an impermeable top film over said lower layer, the top film having opposite longitudinally extending edges; and laterally extendible wings that can be folded and lodged, in a rest position, between said lower layer and said top film in which said wings are releasably attached to said top film, wherein said top film is provided with longitudinally extending adhesive bands which are respectively adjacent to the edges of said top film and which extend along the length of the sanitary napkin, the bands being suitable for attaching at least part of the wings to said film, when the wings are in said rest position, wherein the wings are comprised of respective adhesive regions and wherein protective sheets are included over said lower layer and said sheets are located in such a way that, when the wings are in the rest position, the respective adhesive regions releasably adhere to corresponding ones of said protective sheets.

2. A napkin according to claim 1, in which said top film is provided with weakening lines which permit a portion of the top film that is attached to the wing to detach from an adjacent portion of the top film that is attached to a main body portion of the sanitary napkin.

3. A napkin according to claim 1, in which said top film is shorter than said napkin.

4. A napkin according to claim 1, in which each of the wings is comprised of an extension.

5. A sanitary napkin, comprising:

an upper liquid permeable layer;

a lower liquid impermeable layer;

an absorbent body between said upper and lower layers;

an impermeable top film over said lower layer; and laterally extendible wings that can be folded and lodged, in a rest position, between said lower layer and said top film;

in which said wings are releasably attached to said top film wherein the top film is comprised of longitudinal crimped portions suitable for attaching at least part of the wings to said film when the wings are in said rest position.

6. A napkin according to claim 5, in which said crimped portions extend along the length of the napkin.

* * * * *